(12) United States Patent
Miyata

(10) Patent No.: US 8,974,835 B2
(45) Date of Patent: Mar. 10, 2015

(54) GASTRIC ULCER THERAPEUTIC AGENT

(75) Inventor: Shigeo Miyata, Kitakyushu (JP)

(73) Assignee: Kabushiki Kaisha Kaisui Kagaku Kenkyujo, Fukuoka-Ken (JP)

( * ) Notice: Subject to any disclaimer, the term of this patent is extended or adjusted under 35 U.S.C. 154(b) by 707 days.

(21) Appl. No.: 13/030,261

(22) Filed: Feb. 18, 2011

(65) Prior Publication Data

US 2011/0206779 A1 Aug. 25, 2011

(30) Foreign Application Priority Data

Feb. 19, 2010 (JP) .................................. 2010-034311

(51) Int. Cl.
- *A61K 8/26* (2006.01)
- *A61K 33/08* (2006.01)
- *A61K 33/10* (2006.01)
- *A61K 33/30* (2006.01)

(52) U.S. Cl.
CPC ................. *A61K 33/08* (2013.01); *A61K 33/10* (2013.01); *A61K 33/30* (2013.01)
USPC .......................................... 424/690; 424/686

(58) Field of Classification Search
CPC ....... A61K 33/08; A61K 33/10; A61K 33/30; A61K 8/26
See application file for complete search history.

(56) References Cited

U.S. PATENT DOCUMENTS

| 3,843,778 | A | * | 10/1974 | Diamond et al. | 424/498 |
| 5,935,610 | A | * | 8/1999 | McLean | 424/643 |
| 2003/0087750 | A1 | * | 5/2003 | Stamires et al. | 501/141 |
| 2009/0142394 | A1 | | 6/2009 | Okada et al. | |

FOREIGN PATENT DOCUMENTS

| WO | 2008/075621 | 6/2008 |
| WO | 2009/016349 | 2/2009 |

* cited by examiner

*Primary Examiner* — Abigail Fisher
*Assistant Examiner* — Jessica Kassa
(74) *Attorney, Agent, or Firm* — Wenderoth, Lind & Ponack, L.L.P.

(57) ABSTRACT

A gastric ulcer therapeutic agent comprising as an active ingredient a composite hydroxide of a hydrotalcite and an aluminum hydroxide compound, which composite hydroxide is represented by the formula (1), $$Mg_{1-x}Al_x(OH)_{2+x-ny}(A^{n-})_y(H_2O)_m \qquad (1),$$

wherein $A^{n-}$ represents an anion, n represents a valence of the anion in the range of 1 to 4, x is in the range of $0.34 < x < 0.7$, y is in the range of $0 < y < 0.8$, and m is in the range of $0 < m < 4$.

7 Claims, No Drawings

GASTRIC ULCER THERAPEUTIC AGENT

TECHNICAL FIELD OF THE INVENTION

The present invention relates to a safe and high-function gastric ulcer therapeutic agent comprising as an active ingredient a composite hydroxide of Mg and Al, which is excellent in functions such as gastric mucosa protection.

PRIOR ART OF THE INVENTION

Gastric ulcer is a disease caused by a variety of causes such as stress or crapulence. Because of such causes, a resistance weak portion arises in gastric mucosa and a gastric acid or digestive juice secreted from stomach attacks the mucosa at the resistance weak portion, thereby causing tissue lesion. As therapeutic agents, there are drugs affecting attack factors such as hydrochloric acid or gastrointestinal hormone and drugs affecting protection factors such as mucus, mucosa, blood or bicarbonate ion. Antacids such as aluminum hydroxide gel, magnesium hydroxide or hydrotalcite, H2-blockers such as cimetidine or famotidine and proton pump inhibitors such as omeprazole or lansoprazole are known as inhibitors for the attack factors. As promoters for the protection factors, there are the above-mentioned antacids, gastric mucosa protective covering agents such as sucralfate, cytoprotective agents utilizing zinc ions such as polaprezinc or zinc-containing hydrotalcite, granulation tissue repairing agents such as aldioxa, azulene sulfonic acid or azulene sodium sulfonate, mucus-producing secretomotory agents such as teprenone or gefarnate, and mucosal blood flow improving agents such as cetraxate hydrochloride or rebamipide.

As a recent tendency, a gastric acid antisecretory action is strengthened by proton pump inhibitors, which have evolved from H2-blockers, and as a result the proton pump inhibitors have become a drug of primary choice for ulcer therapy so that the therapeutic effect of the mucosa protection factor promoters has come to be neglected.

Because of the development of the proton pump inhibitors, the enzyme activity of proton pump is inhibited at the final stage of gastric acid secretion so that gastric acid secretion is almost completely prevented and, in addition, it can be prevented for a long period of time or almost one day by taking a dose of proton pump inhibitor. The use of the proton pump inhibitors has remarkably eliminated ulcer attack factors so that the value of existence of the ulcer protection factor agents, a plurality of which have been proposed so far, has declined. Therefore, the proton pump inhibitor is a drug of primary choice for gastric ulcer therapy at the present time.

However, the proton pump inhibitors have a problem in that the recurrence rate of ulcer within one year after the stoppage of the taking of the inhibitors is high, that is, about 50%. Further, there is another problem in that administration of proton pump inhibitor for a long period of time causes excess formation of ECL cell, which produces histamine that stimulates gastric acid secretion, or cavitation of wall cell. Furthermore, there are side effects such as shock, hematopathy or visual disturbance.

SUMMARY OF THE INVENTION

It is an object of the present invention to provide a novel low-toxic gastric ulcer therapeutic agent capable of inhibiting an attack of gastric acid in a safe way without a side effect and exhibiting at least the same therapy effect as that exhibited by a proton pump inhibitor.

The present inventor has deduced that the cause of the above-mentioned side effects of gastric acid secretion inhibitor such as proton pump inhibitors is that while biological mechanism of gastric acid secretion, which is necessary for food digestion and is inherently possessed by human being, is not understood as a whole, only the gastric acid secretion is inhibited. It is supposed that when taking of the inhibitor is stopped, the biological mechanism recognizes the gastric acid secretion inhibition state at the time of taking the inhibitor as a gastric acid secretion malfunction so that an organism provides instructions to increase the amount of gastric acid secretion as compared with before the taking of the inhibitor.

Therefore, when gastric mucosa can be substantially protected from attack of gastric acid by developing an agent capable of covering gastric mucosa for a long time and making gastric acid harmless by means of neutralization instead of utilizing the method of gastric acid secretion biological function inhibition, the same ulcer therapy effect as that provided by the gastric acid secretion inhibitor can be expected. For that purpose, such agent is to have a positively-charged surface, as a result thereof strongly adsorb to gastric mucosa which is negatively charged, also comprise highly-dispersible fine particles capable of covering the whole of a gastric mucosa surface without any space, and also be slowly dissolved in gastric acid.

So-called antacids such as hydrotalcite, aluminum hydroxide gel or magnesium hydroxide cover gastric mucosa, while such antacids are immediately dissolved by gastric acid so that it is impossible to carryout the gastric mucosa covering protection for a long period of time. Sucralfate, which is a gastric mucosa covering protection agent, is negatively charged and adsorbs to protein-derived positively-charged portions existing partially on a gastric surface so that its covering power is insufficient. In addition, it is poor in gastric acid neutralizing ability so that it is insufficient in view of the above purpose.

On the basis of the above thoughts, the present inventor has completed the present invention owing to a longtime research and experience about antacids, etc.

The present invention provides a gastric ulcer therapeutic agent comprising as an active ingredient a composite hydroxide represented by the formula (1), $$Mg_{1-x}Al_x(OH)_{2+x-ny}(A^{n-})_y(H_2O)_m \quad (1)$$

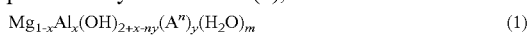

wherein $A^{n-}$ represents an anion having a valence of n, such as $Cl^-$, $SO_4^{2-}$, $CO_3^{2-}$, $HPO_3^{2-}$ or $NH_2CH_2COO^-$, preferably $CO_3^{2-}$, x is in the range of $0.34<x<0.7$, preferably $0.37 \leq x \leq 0.6$, particularly preferably $0.4 \leq x \leq 0.5$, y is in the range of $0<y<0.8$, preferably $0.2<y<0.4$, and m is in the range of $0<m<4$.

EFFECT OF THE INVENTION

The gastric ulcer therapeutic agent of the present invention uses an Mg and Al hydroxide compound which is known to be high in the safety of human organism from the actual past results of longtime use as an antacid and also exhibits a therapy effect higher than that of a proton pump inhibitor having the highest gastric ulcer therapy effect. Further, it does not influence biofunction so that it is free from a side effect such as recurrence after stoppage of administration, which is found with regard to a gastric acid secretion inhibitor such as the proton pump inhibitor.

DETAILED DESCRIPTION OF THE INVENTION

Here, the composite hydroxide refers to a composite of a hydrotalcite represented by the formula (2) and an aluminum hydroxide compound, $$Mg_{1-z}Al_z(OH)_2(A^{n-})_{z/n}(H_2O)_k \quad (2)$$

wherein $A^{n-}$ represents an anion having a valence of n as defined in the formula (1), z is in the range of $0<z\leq0.33$, and k is in the range of $0\leq k<3$.

The term "composite" refers to a state where the whole or part of a crystal surface of the hydrotalcite is covered with the aluminum hydroxide compound. Owing to this composite, the aluminum hydroxide compound retards the dissolution of the hydrotalcite due to gastric acid.

As an antacid belonging to the hydrotalcite, there is a synthetic hydrotalcite of $z=0.25$ and $A^{n-}=CO_3^{2-}$. The aluminum hydroxide compound refers to a crystalline or amorphous aluminum hydroxide represented by the composition formula of $Al(OH)_3$ or AlOOH or basic aluminum carbonate. Examples of the aluminum hydroxide include bayerite, gibbsite, boehmite, etc.

The Al solid solution limit of the hydrotalcite is Mg:Al=2:1. Al which exceeds the above solid solution limit exists in the neighborhood of the crystal surface of the hydrotalcite in the form of amorphous or crystalline $Al(OH)_3$. When such composition is hydrothermally treated at about 150° C. or higher, it converts into a crystal of boehmite or the like and the chemical constitution thereof is AlOOH. The solubility of the aluminum hydroxide compound in gastric acid (pH=about 1) is nil or almost nil. Therefore, the ulcer therapeutic agent of the present invention is characterized by its structure where the aluminum hydroxide compound insoluble in gastric acid covers the crystal surface of the hydrotalcite soluble in gastric acid. As a result, the ulcer therapeutic agent of the present invention can perform the function of not being dissolved in gastric acid for a long time while possessing a gastric acid neutralization ability.

Since the surfaces of both the hydrotalcite and the aluminum hydroxide compound are positively charged, the therapeutic agent of the present invention chemically adsorbs to gastric mucosa which is negatively charged so that the therapeutic agent is excellent in covering protection ability for a gastric mucosa surface.

For covering gastric mucosa efficiently, it is preferred that the therapeutic agent of the present invention comprises fine particles. For example, the average secondary particle diameter thereof is preferably 1 μm or less, particularly preferably 0.5 μm or less.

The therapeutic agent of the present invention can be produced by a conventionally known coprecipitation method. The crystalline aluminum hydroxide can be obtained by heating after the coprecipitation reaction. The heating treatment is carried out at 70° C. or higher, preferably 100° C. or higher, for about 1 to 20 hours, preferably by means of hydrothermal treatment using an autoclave.

For the coprecipitation reaction, an aqueous solution containing water-soluble salts of Mg and Al such as chlorides, nitrates or sulfates and an aqueous solution containing alkali such as sodium hydroxide or sodium carbonate or a mixture of such aqueous solutions containing alkali are reacted with pH kept at 7 or higher, preferably 8.5 to 10.5. Then, usual steps such as washing with sodium carbonate water (in the case of obtaining a $CO_3^{2-}$ type agent), filtering, washing with water, hydrothermal treatment, filtering, drying, pulverization and classification are properly selected and carried out, whereby the therapeutic agent of the present invention can be produced.

The therapeutic agent of the present invention may be used alone or in combination with a zinc ion supplying agent which contributes to cell proliferation, such as zinc oxide, zinc hydroxide, zinc carbonate, a zinc-containing hydrotalcite, and a solid solution of magnesium hydroxide and zinc; (Mg, Zn)(OH)$_2$, or an antacid such as aluminum hydroxide gel or a synthetic hydrotalcite for the purpose of promoting the repair of a cell at an ulcer portion or improving a gastric acid neutralization ability. The amount of the zinc ion supplying agent is preferably 0.01 to 40 parts by weight, more preferably 1 to 10 parts by weight, per 100 parts by weight of the composite hydroxide of the present invention.

The agent form of the therapeutic agent of the present invention can be selected from a variety of usual forms such as suspension, tablet, granule or powder.

EXAMPLES

The present invention will be concretely explained with reference to Examples, hereinafter.

Example 1

A mixed aqueous solution of magnesium chloride and aluminum nitrate (Mg=0.9 mol/L, Al=0.6 mol/L, 30° C.) at a flow rate of 200 mL/minute, a sodium carbonate solution (1.0 mol/L) at a flow rate of 60 mL/minute and a sodium hydroxide aqueous solution (Na=3.0 mol/L) at a flow rate of about 160 mL/minute were supplied to a reaction vessel having a volume of 3 L and having overflow equipment, in which 1 L of water had been placed in advance, with a metering pump with stirring, to carry out a coprecipitation reaction, while the pH of the mixture was kept at about 9.0-9.3 by adjusting the flow rate of the sodium hydroxide aqueous solution. From 20 minutes after overflow, the reaction mixture was recovered for 30 minutes, and it was filtered under reduced pressure, then washed with 6 liters of a sodium carbonate aqueous solution (0.2 mol/L) and washed with water.

The water-washed product was added to water and the resultant mixture was subjected to dispersion treatment with an agitator. Then, part of the resultant mixture was placed in an autoclave and hydrothermally treated at 140° C. for 15 hours. The hydrothermally-treated product was taken out, filtered under reduced pressure, washed with water, dried at about 120° C. for 10 hours and pulverized, thereby producing an intended agent as a powder.

As to the chemical constitution of the agent, the agent was dissolved under heat in perchloric acid and then Mg and Al were analyzed by a chelate titration method. $CO_2$ was analyzed by an AGK style carbon dioxide gas measuring method and a crystal water was analyzed by TG-DTA. The results were as follows.

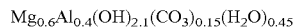

$$Mg_{0.6}Al_{0.4}(OH)_{2.1}(CO_3)_{0.15}(H_2O)_{0.45}$$

As a result of the XRD measurement of the above powder, it was a mixture of a hydrotalcite (main ingredient) and a small amount of bayerite; $Al(OH)_3$. This powder was subjected to ultrasonic treatment in ethanol for 5 minutes, and then measured for particle size distribution by a laser diffraction method. The average secondary particle diameter was 0.5 μm.

Example 2

A powder was obtained in the same manner as in Example 1 except that the aluminum nitrate concentration was changed to 0.9 mol/L and the flow rate of the sodium hydroxide aqueous solution was changed to about 180 mL. The chemical constitution of the powder was as follows.

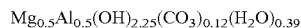

$$Mg_{0.5}Al_{0.5}(OH)_{2.25}(CO_3)_{0.12}(H_2O)_{0.39}$$

As a result of XRD measurement, the powder was a mixture of a hydrotalcite as a main ingredient and a small amount of bayerite. The average secondary particle diameter of the powder was 0.48 μm.

Example 3

A powder was obtained in the same manner as in Example 1 except that the magnesium chloride was replaced with magnesium nitrate (Mg=0.8 mol/L), the aluminum nitrate was replaced with aluminum sulfate (Al=1.2 mol/L) and the temperature of the hydrothermal treatment after the coprecipitation reaction was changed to 120° C. The results of the constitution analysis of the powder were as follows.

$$Mg_{0.4}Al_{0.6}(OH)_{2.4}(CO_3)_{0.1}(H_2O)_{0.3}$$

As a result of the XRD measurement of the powder, the powder was a mixture of a hydrotalcite and bayerite. The average secondary particle diameter of the powder was 1.2 μm.

Comparative Example 1

A powder was obtained in the same manner as in Example 1 except that the magnesium chloride concentration in the mixed aqueous solution of magnesium chloride and aluminum nitrate was changed to Mg=1.0 mol/L and the aluminum nitrate concentration in the mixed aqueous solution was changed to Al=0.5 mol/L. The results of the constitution analysis of the powder were as follows.

$$Mg_{0.68}Al_{0.32}(OH)_2(CO_3)_{0.16}(H_2O)_{0.42}$$

As a result of XRD measurement, the powder was composed of a hydrotalcite alone. The average secondary particle diameter of the powder was 0.51 μm.

Comparative Example 2

A powder was obtained in the same manner as in Example 1 except that the magnesium chloride concentration in the mixed aqueous solution of magnesium chloride and aluminum nitrate was changed to Mg=0.3 mol/L, the aluminum nitrate concentration in the mixed aqueous solution was changed to Al=1.2 mol/L, the flow rate of the sodium carbonate solution was changed to 120 mL/minute, the flow rate of the sodium hydroxide aqueous solution was changed to about 200 mL/minute, and the hydrothermal treatment after the coprecipitation reaction was not carried out. The results of the constitution analysis of the powder were as follows.

$$Mg_{0.2}Al_{0.8}(OH)_{1.3}(CO_3)_{0.05}(H_2O)_{0.15}$$

As a result of XRD measurement, the powder was a mixture of bayerite, gibbsite and a hydrotalcite. The average secondary particle diameter of the powder was 2.8 μm.

[Measurement of Adsorption Amount of Naphthol Yellow S]

1.0 g of a powder sample was added to 500 mL of an aqueous solution of naphthol yellow S (NYS) (concentration 100 ppm). The mixture was stirred at 30° C. for 1 hour and then filtered to obtain a filtrate. The concentration of NYS in the filtrate was measured with a spectrophotometer and the adsorption amount of the sample was obtained.

[Influence on Rat Water Immersion Restraint Stress Ulcer]

The powders obtained in Examples 1, 2 and 3, a mixed powder containing the powder obtained in Example 2 and basic zinc carbonate (Zn=58%), the powders obtained in Comparative Examples 1 and 2, lansoprazole as a proton pump inhibitor and sucralfate, which is most highly evaluated as a gastric mucosa protective agent, were used as test specimens. These test specimens were examined for effect on water immersion restraint stress ulcer, which is an acute ulcer model.

Eight Wister rats as a group were preliminarily reared for a few days. The rats were fasted for 24 hours. Then, the rats were placed in a stress cage according to the method of Takagi et al. (Jap, J, Pharacol, 18:9, 1968). The rats were immersed up to xiphoid process parts in a water tank having a temperature of 23° C. and the rats were subjected to stress for 7 hours. Then, their stomachs were taken out under ether anesthesia. About 12 mL of 2% formalin physiological saline solution was injected into each stomach, to fix the stomach. Then, each stomach was cut out along a curvatura ventriculi major side. The length (mm) of mucosa ulcer at a glandular stomach portion was measured.

As to oral administration of the test specimens, 5 mL/kg (rat weight) of a liquid containing a test specimen was administered 30 minutes before the load of the stress. In Control, the same amount of water was administered. Table 1 shows the results thereof together with antacid power, measured according to the pharmacopoeia of Japan, and the adsorption amount of NYS.

TABLE 1

| Test specimen | Dosage (mg/kg) | NYS adsorption amount (mg/g) | Antacid power (mL/g) | Length of gastric mucosa impairment (mm) | Inhibition rate (%) |
|---|---|---|---|---|---|
| Control | — | — | — | 14.7 | |
| Example 1 | 500 | 6.42 | 234 | 1.6 | 89 |
| Example 2 | 500 | 5.16 | 241 | 1.2 | 92 |
| Example 2 Basic zinc carbonate | 500 30 | | 246 | 0.7 | 95 |
| Example 3 | 500 | 4.15 | 218 | 2.8 | 81 |
| Comparative Example 1 | 500 | 6.45 | 297 | 5.3 | 64 |
| Comparative Example 2 | 500 | 2.14 | 145 | 8.1 | 45 |
| Sucralfate | 500 | 0.60 | 168 | 4.3 | 71 |
| Lansoprazole | 40 | 0 | 0 | 3.2 | 78 |

Dosage: the applied dose of a test specimen per 1 kg of the weight of a rat.
NYS: NYS adsorption amount means that as the NYS adsorption amount is larger, the positive charge amount of a test specimen becomes higher.

Table 1 shows that the agents of the present invention were excellent in gastric ulcer therapy effect over sucralfate, which is said to be most excellent as a gastric mucosa protective agent, and the proton pump inhibitor. Table 1 also shows that the excellent gastric ulcer therapy effect of the agents of the present invention was based on strong adsorptive power to gastric mucosa, i.e., covering power, which was known from the high NYS adsorption amounts, and the moderately high antacid power.

What is claimed is:

1. A gastric ulcer therapeutic agent comprising as an active ingredient a composite hydroxide of a hydrotalcite and an aluminum hydroxide compound, which composite hydroxide is represented by the formula (1), $$Mg_{1-x}Al_x(OH)_{2+x-ny}(A^{n-})_y(H_2O)_m \qquad (1),$$

wherein $A^{n-}$ represents an anion, n represents a valence of the anion in the range of 1 to 4, x is in the range of $0.4 < x < 0.7$, y is in the range of $0 < y < 0.8$, and m is in the range of $0 < m < 4$; and wherein the hydrotalcite is partially or entirely covered with the aluminum hydroxide compound.

2. The gastric ulcer therapeutic agent according to claim 1, wherein the aluminum hydroxide compound is boehmite.

3. The gastric ulcer therapeutic agent according to claim 1, wherein x in the formula (1) is in the range of $0.37 \leq x \leq 0.6$.

4. The gastric ulcer therapeutic agent according to claim 1, wherein $A^{n-}$ in the formula (1) represents $(CO_3)^{2-}$.

5. The gastric ulcer therapeutic agent according to claim 1, wherein $A^{n-}$ in the formula (1) represents glycine.

6. The gastric ulcer therapeutic agent according to claim 1, wherein the composite hydroxide represented by the formula (1) has an average secondary particle diameter of 1 μm or less.

7. The gastric ulcer therapeutic agent according to claim 1, wherein the gastric ulcer therapeutic agent further comprises 0.01 to 40 parts by weight of at least one zinc compound selected from the group consisting of zinc oxide, zinc hydroxide, zinc carbonate, basic zinc carbonate, organic acid zinc, basic organic acid zinc and inorganic acid zinc, per 100 parts by weight of the composite hydroxide of the formula (1).

\* \* \* \* \*